United States Patent [19]

Ersek

[11] Patent Number: 4,592,357
[45] Date of Patent: Jun. 3, 1986

[54] SEPTAL SPLINT

[76] Inventor: Robert A. Ersek, Park St. David, 800 E. 30th St., Ste. 309, Austin, Tex. 78705

[21] Appl. No.: 651,475

[22] Filed: Sep. 17, 1984

Related U.S. Application Data

[63] Continuation-in-part of Ser. No. 442,592, Nov. 18, 1983, Continuation-in-part of Ser. No. 265,963, May 21, 1981, Pat. No. 4,378,802.

[51] Int. Cl.⁴ .............................................. A61F 5/04
[52] U.S. Cl. .................................................... 128/342
[58] Field of Search ............... 128/342, 343, 346, 325, 128/76 R, 76 C, 89 R, 89 C, 89 A

[56] References Cited

U.S. PATENT DOCUMENTS

| | | | |
|---|---|---|---|
| 2,691,985 | 10/1954 | Newsom | 128/342 |
| 3,349,771 | 10/1967 | Baer | 128/325 |
| 3,935,859 | 2/1976 | Doyle | 128/342 |
| 4,105,035 | 8/1978 | Rella | 128/342 |

FOREIGN PATENT DOCUMENTS 2419711 11/1979 France ............................... 128/342

Primary Examiner—Jay N. Eskovitz
Attorney, Agent, or Firm—Orrin M. Haugen; Thomas J. Nikolai

[57] ABSTRACT

An improved septal splint for maintaining the nasal septum in a desired orientation following reconstructive surgery. The composite splint includes two symmetrical halves, each including a plate member having a planar surface for contacting the septum and a tubular passageway for facilitating nasal breathing during the healing process. In another embodiment, an elastic expander or balloon is secured to each of the splint members such that following their insertion into the nasal orifices, the balloons can be inflated to apply predetermined pressures to each side of the septum. The impregnation of the septum contacting surface of the splint with a hemostatic agent and/or the lining or fabrication thereof from impregnated porcine skin are also contemplated.

5 Claims, 16 Drawing Figures

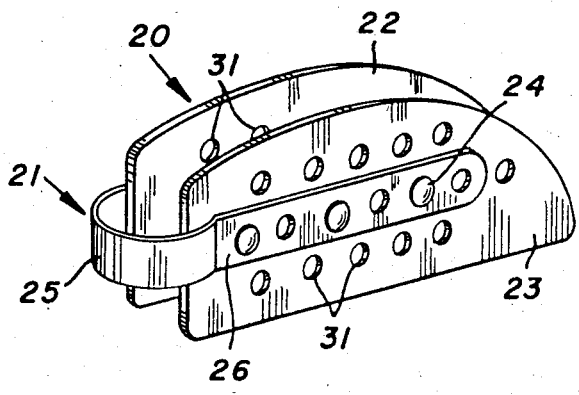
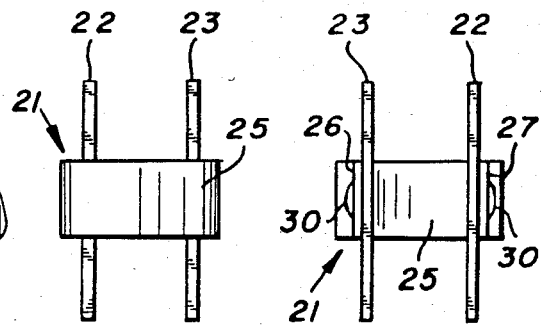
FIG. 1    FIG. 2    FIG. 3
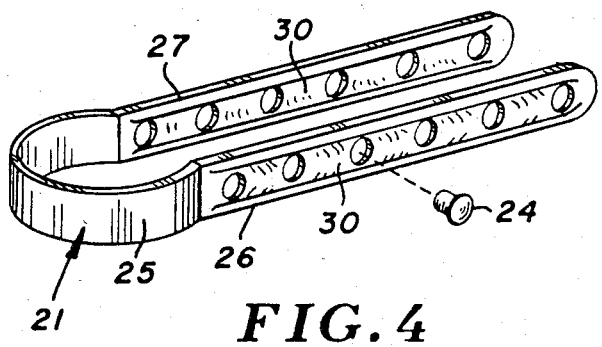
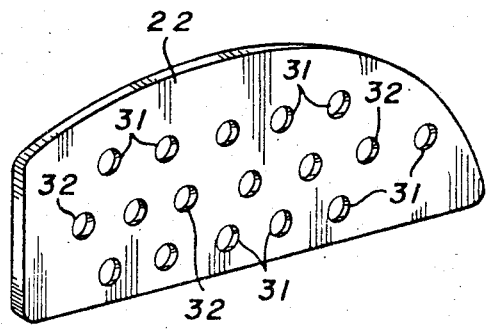
FIG. 4    FIG. 5
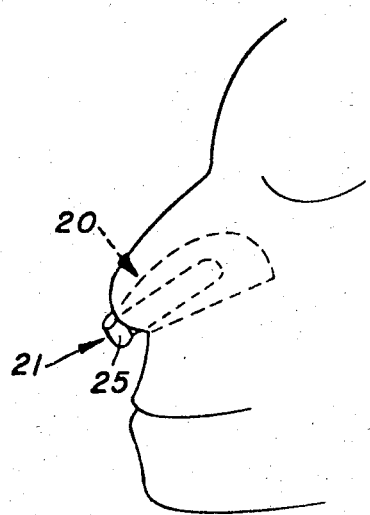
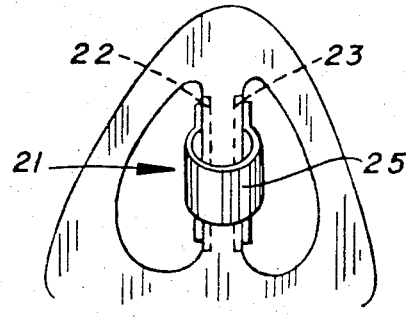
FIG. 6    FIG. 7

SEPTAL SPLINT

CROSS-REFERENCE TO RELATED APPLICATIONS

This is a continuation-in-part of application Ser. No. 442,592, filed Nov. 18, 1983, which is a continuation-in-part of application Ser. No. 265,963, filed May 21, 1981, now U.S. Pat. No. 4,378,802.

FIELD OF THE INVENTION

This invention relates the field of surgery, and more particularly to surgery directed to the repair of injuries or defects in the human nasal septum.

BACKGROUND OF THE INVENTION

In the practice of nasal reconstructive surgery, it is often necessary to provide support to the septum of the nose. This may be done merely by packing the nose with gauze or inflatable balloons, but these expedients do not ensure that the septum itself will be supported, or will remain straight or symmetrical. Another technique includes cutting pieces of a material such as polyethylene sheet to the shape of the septum on both sides, placing the pieces within the nostrils, and passing transfixion stitches through the septum and the two pieces of material in order to provide an external framework for the septum. This procedure sometimes results in necrosis of the septum or its mucosal lining, or accumulation of blood or mucus under the plastic pieces. It also frequently occurs that removal of the stitches and the plastic pieces causes disruption of recently-repaired tissues, and can be made difficult by crusting or adhesion.

SUMMARY OF THE INVENTION

The present invention comprises a splint which can be inserted into the nose to apply moderate pressure to both sides of the septum without exceeding capillary pressure, which is aesthetically acceptable to the patient, and which is readily removable when its use is no longer needed. In one embodiment the split comprises a pair of generally rigid plate members which are shaped to define a desired septal outline and which are adapted to be disposed on either side of the nasal septum within the two nasal fossae. Each of the plates is provided with a pattern of apertures to facilitate the passage of mucus. In that embodiment, a clip member may optionally be used to maintain the two plate members in a desired alignment, the clip member also being perforated to allow for drainage as well as to accommodate a suitable fastener adjoining it to its associated plate members.

In an alternative embodiment, the plate members are provided with an integrally formed portion providing an air passageway to insure a free passage of air even when packing is employed in conjunction with the nasal splint.

In still another variation, an inflatable balloon member may be formed as a part of the septal splint such that when the individual halves thereof are inserted into the nasal fossae and the balloon is inflated, the pressure exerted against the interior wall surfaces of the nasal passage by the balloon will maintain the splint in a desired orientation relative to the nasal septum itself. Again, it is preferable in this arrangement to incorporate the integrally formed air passageway as a part of the splint to allow the patient to breathe through the nose when the splint is in position.

In yet still another variation of the present invention, it is desirable to impregnate the plate members with a hemostatic agent, such as collagen or gelatin or alternatively, cover the plate members with an impregnated zenograph skin and/or fabricate the plate members from an impregnated skin product. In this way, bleeding can be controlled in conjunction with the desirable features of the foregoing embodiments.

Various advantages and features of novelty which characterize the invention are pointed out with particularity in the claims annexed hereto and forming a part hereof. However, for a better understanding of the invention, its advantages, and objects obtained by its use, reference should be had to the drawing which forms a further part hereof, and to the accompanying descriptive matter, in which there is illustrated and described a preferred embodiment of the invention.

BRIEF DESCRIPTION OF THE DRAWING

In the drawing, in which like reference numerals indicate corresponding parts throughout the several views, FIG. 1 is a perspective view of a splint according to the invention;

FIGS. 2 and 3 are end views of the splint of FIG. 1 seen from the left and right respectively;

FIGS. 4 and 5 are view in perspective of a clip member and a plate member which are portions of one form of the invention;

FIG. 6 is a lateral view of a splint in place, shown schematically;

FIG. 7 is a nostril view showing a splint in place;

DESCRIPTION OF THE PREFERRED EMBODIMENT

Figure 8:
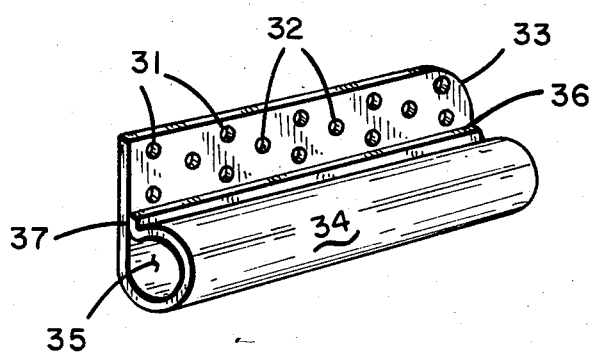
FIG. 8 is a perspective view of an alternative embodiment of a plate member comprising a portion of the septal splint.

A septal splint 20 according to one embodiment of the invention is shown in FIG. 1 to comprise a clip member 21 and a pair of plate members 22 and 23 connected to the clip member by fasteners such as rivets 24. Clip member 21 is formed of a strip of material such as aluminum having a central loop 25 from which a pair of parallel struts 26 and 27 extend in the same direction, the struts being spaced by less than the diameter of the loop which extends peripherally through more than 180°. If desired, the material of loop 25 may be wider than that of struts 26 and 27, which struts may also be reinforced by ribs 30. The struts include a plurality of drainage holes having a predetermined spacing therebetween.

Plate members 22 are preferably of plastic or metal or other body compatible material and thick enough to be reasonably rigid yet easily shaped with shears or scissors to the desired septal outline. They are provided with fields of apertures 31 for passage of sutures or for drainage, and with further apertures 32 to receive rivets 24 by which the plate members may be secured to the inner surfaces of struts 26 and 27. Polyethylene is suitable for use in plates 22, as it is smooth, easily shaped, and benign and non-adhesive to human tissues. The spacing between holes 31 corresponds to the spacing between holes in the struts to provide unobstructed drainage paths, all as illustrated in FIG. 1.

In use, the splint is sterilized and placed in the nose after reconstructive surgery has been completed, by spreading the clip member, passing the plates into the nose on opposite sides of the septum, and allowing the clip to return to its preformed shape. Loop 25 is large enough to encircle the patient's columella, and the spacing between plates 22 is such, three millimeters, for example, as to apply moderate pressure, to both sides of the septum, sufficient to give adequate support and yet not in excess of capillary blood pressure (25 mm of mercury). Drainage apertures 31 prevent the accumulation of blood or mucus under the plates, and also enable the insertion of transfixion stitches if this procedure is elected. The patient's nostrils may thereafter be packed with gauze if desired.

It will be evident that after application, the splint is only minimally noticeable, a significant aesthetic consideration. When it is desired to remove the splint, loop 25, which remains external, is grasped with a surgical instrument or the fingers of the surgeon, and the loop is cut with surgical scissors, releasing the pressure on the septum and facilitating the removal of the two plate members independently, thus minimizing any trauma of removal.

It is not essential to the proper application of the septal splint of the present invention that the central clip 21 of FIG. 4 be used. The two plate members 22 and 23 may be inserted into the nasal openings and held in position against the septum by means of suitable packing or, alternatively, one or more transfixion stitches passing through the septum may be used to maintain the plate members in position for a desired period of time following nasal reconstructive surgery.

Following reconstructive surgery on the nose, it has been heretofore common practice to use cotton packing to maintain the desired shape configuration of the septum during the healing process. When this approach is employed, breathing through the nasal passages is precluded. Even when the nasal splint of the embodiment of FIGS. 1 through 7 is employed, internal swelling of the tissue may partially or completely obstruct the air passageways in the nose. To facilitate the flow of air through the nasal passages, it has been found to expedient to reconfigure the plate members of FIG. 5 in the fashion indicated in FIGS. 8 through 10 of the drawings. More specifically, in accordance with the embodiment of FIGS. 8 through 10, the plate members 33, while being generally planar over a predetermined length and height dimension terminate in integrally formed rolled segments 34 defining a generally tubular airway 35. The segment 34 is curved sufficiently so that the lowermost edge thereof 36 abuts the outer surface of the plate member 33. Depending upon the particular material employed in the fabrication of the plate member 33 with its integrally formed airway, the edge 36 may be suitably bounded to the exterior surface of the plate member 33 by adhesive, welding or other fastening device along a seamline 37.

Figure 9:
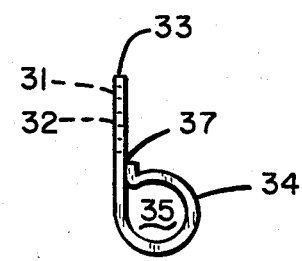
FIG. 9 is an end view of the septal splint of FIG. 8.
Figure 10:
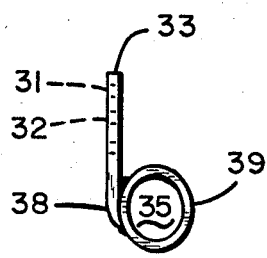
FIG. 10 is an end view of the septal splint plate member incorporating a performed discreet tubular airway.

As in the embodiment of FIGS. 1 through 7, the embodiment of FIGS. 8 through 10 includes a pattern of drainage apertures 31 and alignment apertures 32 formed through the thickness dimension of the plate member 33. It is preferable that the integrally formed tubular airway portion 34 of the plate member be void of such drainage holes so as to prevent the collection or formation of mucus plugs therein.

The embodiment of FIG. 10 is similar in concept to the septal splint of FIGS. 8 and 9, but illustrates a design in which the tubular airway and the plate member are separate pieces but are bounded or otherwise attached one to the other. That is to say, rather than forming a tubular passage by suitably folding back a portion of the plate member upon itself as shown in FIGS. 8 and 9, a generally planar plate member 38 having drainage apertures 31 and alignment apertures 32 formed therethrough may be bounded or otherwise affixed to a preformed tube member 39 with the two elements being bounded one to the other by an adhesive, by welding or other suitable attachment process determined by the type of materials employed.

It is readily apparent to those skilled in the art that the septum splint plate member of the type depicted in FIGS. 8 and 10 can be placed in each nostril with the flat portions of each positioned on either side of the septum and with a suitable packing material being inserted into the nasal passages at the location exterior to the lumen 35. The packing will serve to hold the plate members against the septum with a predetermined pressure while air is free to pass through the lumen 32 during inspiration and expiration.

Figure 11:
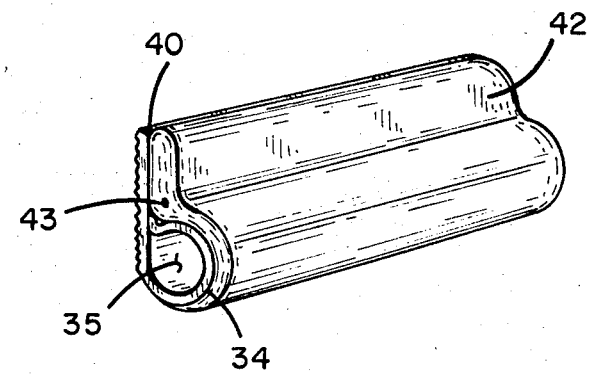
FIG. 11 is a perspective view of a further alternative embodiment of the invention incorporating an expandable balloon member.
Figure 12:
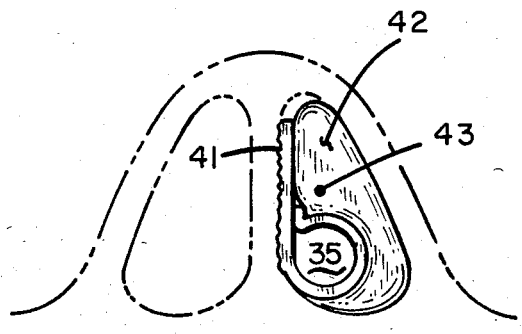
FIG. 12 is a nostril view showing the embodiment of FIG. 11 in place.
Figure 13:
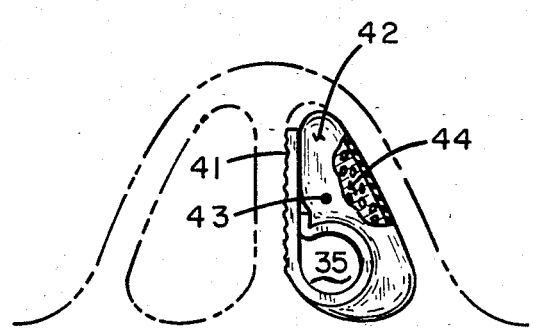
FIG. 13 is a nostril view showing nasal splint incorporating a compressible medium.

To obviate the need of additional packing to hold the plate members in position against the septum, a still further alternative embodiment as depicted in FIGS. 11 through 13 of the drawings may be used. In these views there is disclosed what may be termed a "pressure airway septal splint" or PASS. In this arrangement each half of the PASS includes a plate member 40 which is preferably void of drainage and alignment apertures but having a roughened surface 41 on its septal apposing face, the roughened surface comprising a pattern of serrations, cross-hatching, knurling or checkering. The plate member 40 is also provided with an airway member 34 as in the embodiments of FIGS. 9 and 10 and in addition, preferably includes an expander or balloon member 42 in the form of a latex or other distensible elastic material which is bonded to the exposed surfaces of the plate member along peripheral seams. Each expander member also includes a filling valve 43 which may comprise an easily penetrable, self-sealing material such as silicone rubber. By passing a hypodermic needle (not shown) through the filling valve 43, air or some other suitable fluid may be injected into the ballon member to cause it to be inflated. When the needle is withdrawn, the point of penetration closes to prevent deflation.

With reference to FIG. 12, two of the PASS devices of FIG. 11 are inserted into the patient's nostrils such that the roughened surface 41 thereof are each in intimate contact with the nasal septum and on either side thereof. Once the plate members 40 are inserted, the physician may insert a hypodermic needle through the self-sealing filling valve 43 to inject an inflating medium so as to cause the balloon member 42 to expand and thereby apply a predetermined pressure forcing the roughened planar surface of the plate member 40 firmly against the septum. By properly controlling the relative pressures within the expander members on either side of the septum, the physician may insure that the septum will be held in a midline position to yield a desired symmetry to the nose following reconstructive surgery. As in the embodiment of FIGS. 9 and 10, the air passageway or lumen 35 insures that the patient may breathe even when the balloon member is in its expanded condition.

As illustrated in FIG. 13, it is further contemplated, that instead of providing an expander member of the type which may be inflated after the PASS is inserted into each of the nasal passages, that the expandable bladder 42 may be filled with an open cellular compressible sponge element 44. In installing such a device, a hypodermic needle may again be inserted through the valve 43 and suction applied to thereby evacuate the balloon 42 compressing the sponge 44 and allowing the device to be installed in the nostril. Following such installation, the needle may be connected to atmospheric pressure, allowing the sponge to expand by drawing air into the ballon. The sponge thus expands to conform to the shape of the inside of the nose.

It is expected that persons skilled in the art of fabricating parts from plastic will readily visualize ways of attaching the balloon or expander member to the non-septum contacting surfaces of the plate member and, accordingly, it should suffice to say that injection molding of plastic and subsequent bonding of a preformed silicone rubber or latex sheet having a predetermined thickness profile thereto can readily be accomplished. By properly controlling the thickness profile, a predetermined orientation or shape upon the expansion thereof can be achieved.

Figure 15:
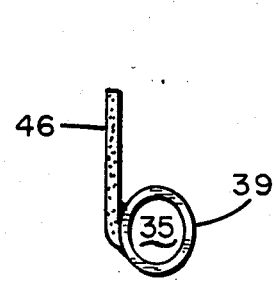
FIG. 15 shows a splint plate member, like that of FIG. 10, having a medicant impregnated plate member.
Figure 14:
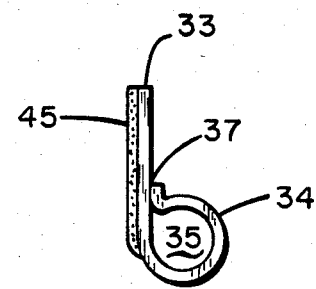
FIG. 14 shows a splint plate member, like that of FIG. 9.
Figure 16:
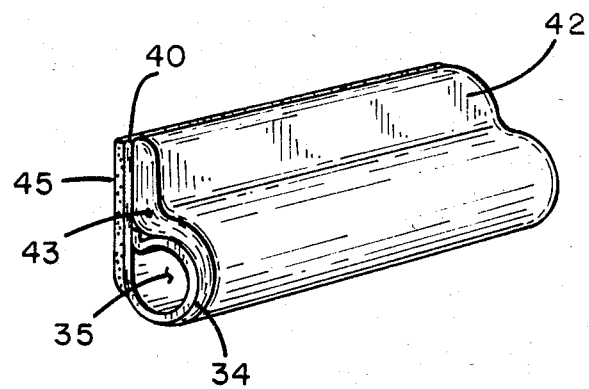
FIG. 16 shows a splint member, like that of FIG. 11, with a medicant impregnated septum contacting layer.

As still further illustrated in FIGS. 14, 15 and 16, it is contemplated that the septum contacting surface of the plate members might also contain a hemostatic agent to control bleeding. In that regard and directing attention to FIG. 14, a layer 45 impregnated with or comprising a hemostatic agent, for example collagen, gelatin, thrombin or sponge is shown in bonded relation to an airway containing plate member 33 of the type disclosed in FIGS. 8 to 10. While various impregnated dressings may be employed as the layer 45, a preferred carrier for such hemostatic agents is fabricated from porcine skin, such as sold by Genetic Laboratories, Inc. of St. Paul, Minnesota in its line of Mediskin TM porcine skin dressings. Such dressings have been proven to facilitate healing and in combination with the aforesaid hemostatic agent would check bleeding. In addition, the material may also be impregnated with a silver ion releasing compound to add antimicrobial properties to the septal splint.

FIG. 15 depicts yet another embodiment, like that of FIG. 10, but wherein the plate member 46 is fabricated solely from an impregnated porcine skin and to which the airway 35 containing tube member 39 is separately attached. For this embodiment, it is also to be recognized that while some rigidity may be obtained by using relatively thick impregnated porcine skin for the plate member 46, in actual practice in a splint the dimensions and materials, adhesives, packing, whether or not drainage and alignment apertures 31 and 32 were included, etc. would typically be adjusted to provide the proper pressure and support and facilitate healing.

FIG. 16 depicts still another plate member 47, like that of FIG. 11, wherein the plate member 40 includes a hemostatic and antimicrobial agent impregnated layer 45 and to the airway 35 containing rolled segment 34 of which is attached a valve 43 filled balloon member 42. Additionally, it is to be recognized that the balloon member 42 could also be added to the plate member 46 to FIG. 15 and/or the airway member 39 thereof.

From the above, it will be evident that the invention comprises a septal splint which is easily shaped to fit a particular need, conveniently applied, self-retaining or suturable as desired, and which supports the septum with a minimum likelihood of necrosis, infection, encrustment or adhesion, a minimum likelihood of bleeding and with maximum ease of removal without trauma.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

What is claimed is:

1. A septal splint for maintaining the nasal septum in planar alignment following a reconfiguration thereof, comprising in combination:
   (a) a pair of generally rigid plate members, each of said plate members having two major side surfaces, one of said side surfaces being roughened to enhance its tissue gripping characteristics;
   (b) an evacuable, contractable bag member containing an opened celled sponge, said bag member being attached to the other of said two major surfaces of each of said plate members;
   (c) tubular airway means extending the length of each of said pair of plate members, said tubular airway means being attached to said plate members and at least partially surrounded by said bag member;
   (d) means for evacuating said bag members to thereby compress said sponges prior to placement of said pair of plate members within the nasal openings with said roughened surfaces abutting the septum to be aligned; and
   (e) means for exposing the interior of said bag members to atmospheric pressure, allowing said sponges to expand following placement of said pair of plate members within said nasal openings whereby the roughened surface of said pair of plate members are held in contact with the septum of either side thereof with a predetermined force.

2. The septal splint as in claim 1 wherein said one surface of each of said plate members is covered with a medium incorporating a hemostatic agent.

3. The septal splint as in claim 2 wherein said medium is pigskin.

4. The septal splint as in claim 2 wherein said medium also incorporates an anti-microbial agent.

5. The septal splint as in claim 1 wherein means for evacuating said bag member includes a self-sealing, penetrable valve disposing in the bag member.

* * * * *

UNITED STATES PATENT AND TRADEMARK OFFICE
CERTIFICATE OF CORRECTION

PATENT NO. : 4,592,357
DATED : June 3, 1986
INVENTOR(S) : Robert A. Ersek

It is certified that error appears in the above-identified patent and that said Letters Patent are hereby corrected as shown below:

Column 6, Line 66, "disposing" should read -- disposed --.

Signed and Sealed this

Twelfth Day of August 1986

[SEAL]

Attest:

DONALD J. QUIGG

Attesting Officer

Commissioner of Patents and Trademarks